(12) United States Patent  (10) Patent No.: US 9,060,869 B1
Glisan  (45) Date of Patent: Jun. 23, 2015

(54) TENSION RING APPLICATOR ASSEMBLY

(71) Applicant: Duane Glisan, St. Louis Park, MN (US)

(72) Inventor: Duane Glisan, St. Louis Park, MN (US)

( * ) Notice: Subject to any disclaimer, the term of this patent is extended or adjusted under 35 U.S.C. 154(b) by 0 days.

(21) Appl. No.: 14/335,052

(22) Filed: Jul. 18, 2014

(51) Int. Cl.
*A61F 5/00* (2006.01)
*A61F 5/41* (2006.01)

(52) U.S. Cl.
CPC ............ *A61F 5/41* (2013.01); *A61F 2005/411* (2013.01)

(58) Field of Classification Search
CPC A61F 5/41; A61F 2005/411; A61F 2005/414
USPC ...................................... 600/38–41
See application file for complete search history.

(56) References Cited

U.S. PATENT DOCUMENTS

| 4,539,980 | A | | 9/1985 | Chaney |
| 4,628,915 | A | | 12/1986 | Chaney |
| 5,083,556 | A | * | 1/1992 | Osbon et al. ............ 600/39 |
| 5,195,943 | A | | 3/1993 | Chaney |
| 5,460,594 | A | * | 10/1995 | Walling .............. 600/38 |
| 5,695,444 | A | | 12/1997 | Chaney |
| 5,997,470 | A | * | 12/1999 | Coates ............. 600/41 |
| 7,828,719 | B2 | | 11/2010 | Michaely |

* cited by examiner

*Primary Examiner* — John Lacyk
(74) *Attorney, Agent, or Firm* — Thomas W. Galvani, P.C.; Thomas W. Galvani

(57) ABSTRACT

An assembly for applying a tension ring to a penis includes an elongate base having a top and a flange just below the top. An applicator is releasably coupled to the top of the base. The applicator has a projecting tab which is smaller than the diameter of the tension ring. The applicator and the base cooperate to define a channel between the tab and the flange which is sized to receive the tension ring. A user can easily apply the tension ring over the tab and then stretch the tension ring over the entire applicator into the channel, whereupon the applicator is moved off the base and onto an erect penis so that the tension ring can be moved from the applicator onto the penis.

22 Claims, 6 Drawing Sheets

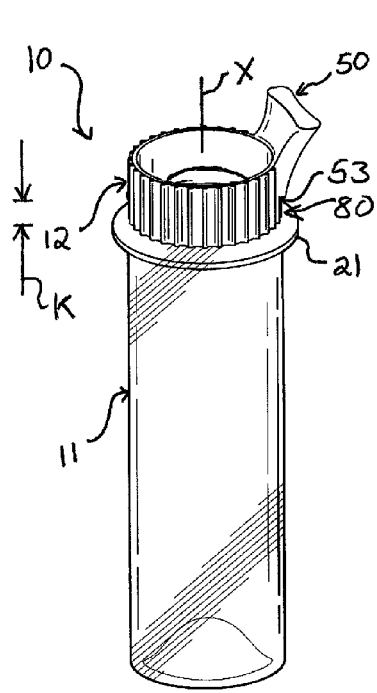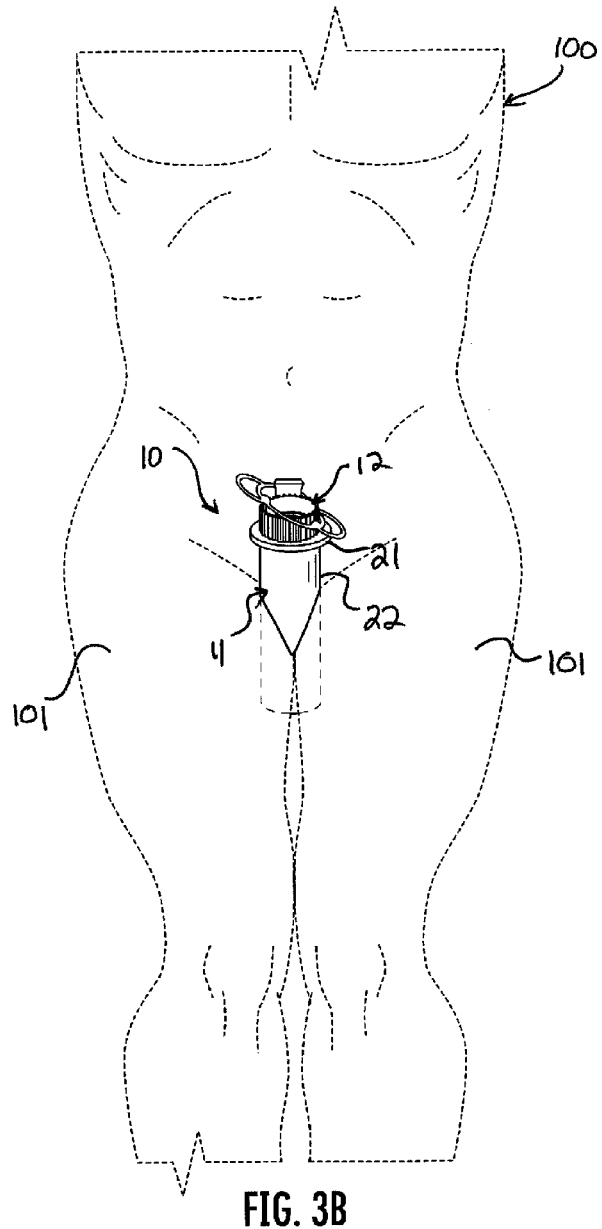
FIG. 3A
FIG. 3B

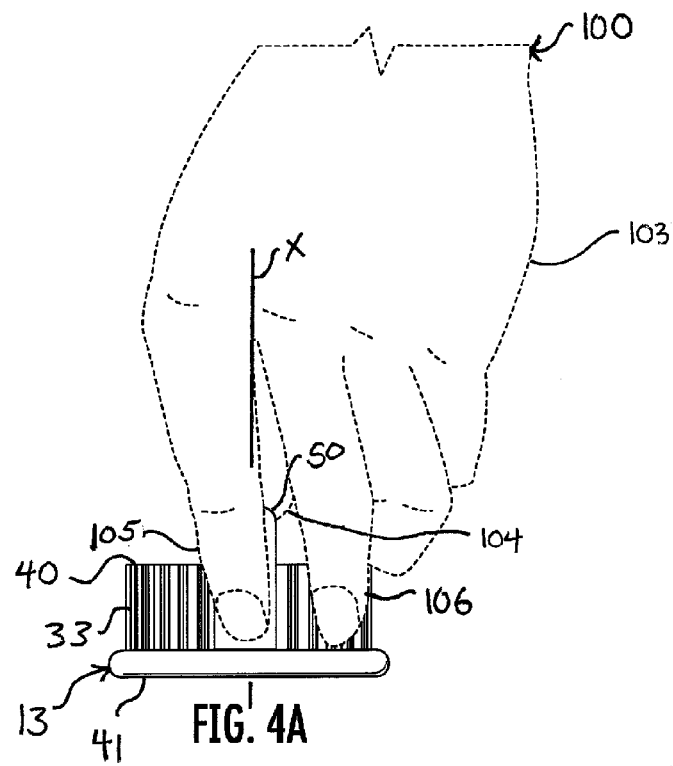
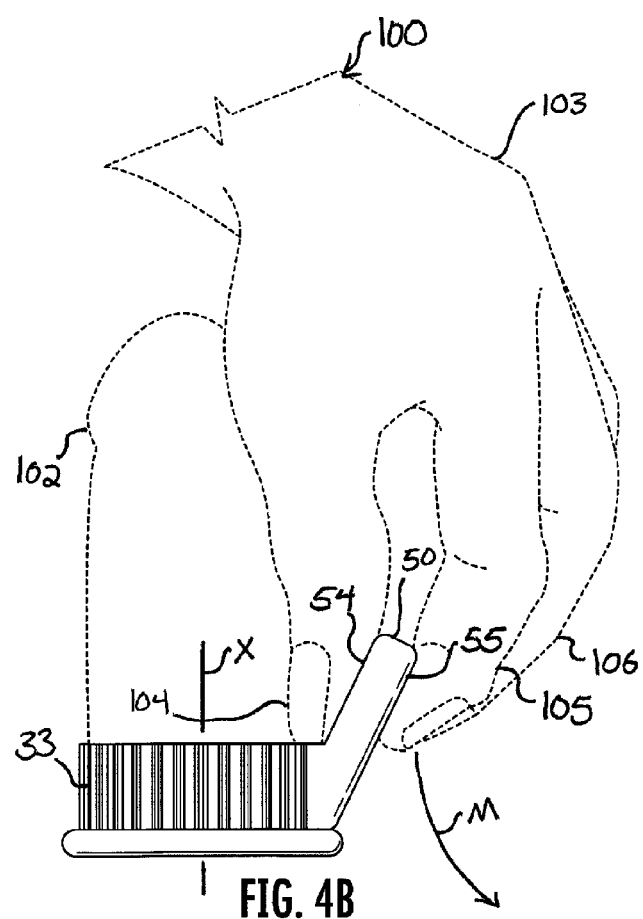

TENSION RING APPLICATOR ASSEMBLY

FIELD OF THE INVENTION

The present invention relates generally to sexual aids, and more particularly to devices for maintaining an erection.

BACKGROUND OF THE INVENTION

Erectile dysfunction exhibits as the inability to develop or maintain an erection. There are a variety of reasons why a man may experience erectile dysfunction during his life. He may be old, stressed, have low testosterone, an anatomical defect, nerve damage, medication side effects, diabetes, prostate cancer, or lasting complications from surgery which causes the problem. Regardless of the cause, the inability to develop or maintain an erection can be stressful, embarrassing, and may lead to a loss of enjoyment of life.

Numerous attempts, mechanical and pharmaceutical alike, have been made to solve both types of erectile dysfunction. Drugs like Viagra®, Cialis®, and Levitra® have had much success for men who cannot develop an erection. Those who can develop an erection, however, strongly desire to maintain it through a full sexual encounter. Venuous constriction rings are one solution for maintaining an erection. Venuous constriction rings, known more colloquially as compression rings, constriction rings, or tension rings (as they are referred to in this description) are a well-known solution for maintaining an erection. A tension ring can be applied to an erect penis to maintain the erection for sexual performance.

A tension ring is a resilient, elastic ring constructed of rubber, silicon, plastic or other similar resilient material that creates an inward constictive force. The tension ring is placed around and against the base of the penis and acts to minimize the amount of blood flowing out of the penis by constricting the penis tightly. Many tension rings have handles or grasping loops to aid in applying the tension ring to an erect penis, because the material is often very difficult to stretch.

Because the tension ring can be difficult to stretch, it can be quite hard to apply to an erect penis. Stretching and sliding the tension ring over an erect penis is difficult because the ring is small and resilient. Further, it is often applied in the middle of a sexual encounter. The stress and awkwardness of applying the tension ring can cause the user to lose his erection before he has had a chance to apply the tension ring. In some cases, it can slip off the penis as it is being applied if the user loses his grip on it.

Various devices and accessories have been developed to assist a man in applying a tension ring. Cones, pumps, and other devices can aid in applying a tension ring. However, these devices generally involve a great deal of planning and preparatory work, and they can be awkward to use in the heat of a sexual moment. Pulling out a medical apparatus in the middle of a sexual encounter can reduce the romance of the encounter for both parties. Further, many of these devices are cumbersome to use, and can require awkward handling of the implement, the tension ring, and the user's own penis. An improved way to maintain an erection is needed, preferably one which is minimally disruptive of the sexual experience for both the user and his partner, which is easy to use, and which is effective.

SUMMARY OF THE INVENTION

According to the principle of the invention, an assembly for applying a tension ring to a penis includes a base having a bottom, an opposed top, a sidewall extending therebetween, and a flange extending outward from the sidewall proximate to the top. An applicator is configurable between an applied condition releasably coupled to the top of the base and a free condition away from the base. The applicator has a bottom, an opposed top, and a sidewall extending therebetween and bounding an open interior sized to receive a penis. In the applied condition of the applicator, the applicator and base cooperate to define a channel formed by and between the applicator and the base which is sized to receive the tension ring therein for application to the applicator. In the free condition of the applicator, the applicator is available to be slid over a penis while carrying the tension ring for application of the tension ring to the penis, and the tension ring is then moved off of the applicator and onto the penis for use.

BRIEF DESCRIPTION OF THE DRAWINGS

Referring to the drawings:

FIGS. 3A-3F illustrate a sequence of steps of applying the tension ring of FIG. 1A onto the tension ring applicator assembly of FIG. 1A and then onto an erect penis; and FIGS. 4A and 4B are front and side elevation views, respectively, illustrating a preferred grip arrangement of the applicator of FIG. 1A.

DETAILED DESCRIPTION

Figure 1A:
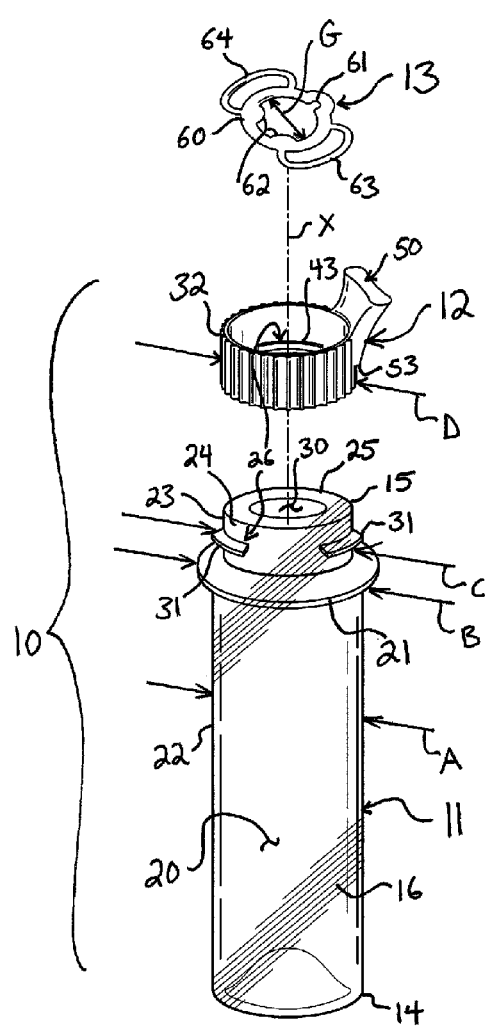
FIG. 1A is an exploded perspective view of a tension ring and a tension ring applicator assembly constructed and arranged according to the principle of the invention, including an applicator and a base.

Reference now is made to the drawings, in which the same reference characters are used throughout the different figures to designate the same elements. FIG. 1 illustrates a tension ring applicator assembly 10 (hereinafter, the "assembly") constructed and arranged according to the principle of the invention, and including an elongate base 11 and an applicator 12 configurable between an applied condition releasably coupled to the base 11 and a free condition away from the base 11. FIG. 1 illustrates the applicator 12 in the applied condition, though in an exploded view. The assembly 10 is a mount over which a tension ring 13 is stretched and applied in anticipation of quick and easy application onto a penis. The assembly 10 is structured to be held between the legs during application of the tension ring 13 to the applicator 12, the applicator 12 can then be removed and slid over the penis, and the tension ring 13 is then transferred from the applicator 12 to the penis as will be explained in detail later. The assembly 10 allows these actions to be taken quickly and in only a few motions, thus assuring that the tension ring 10 can be applied to an erect penis before the erection subsides. Loading the tension ring 13 onto the applicator 12 prior to intimacy is nevertheless often a more desirable choice, however.

The base 11 of the assembly 10 is an elongate, cylindrical body having a bottom 14, an opposed top 15, and a continuous, cylindrical sidewall 16 extending therebetween. The bottom 14, top 15, and sidewall 16 cooperate to bound and define an interior 20 of the base 11 which is sized to store multiple tension rings 13 for later use. The base 11 is preferably constructed of a material or combination of materials having rigid and lightweight material characteristics, such as plastic, and the sidewall 16 of the base 11 is transparent so that tension rings 13 stored in the interior 20 can be seen. The bottom 14 of the base 13 is concave, extending into the interior 20 slightly so that tension rings 13 do not collect and become caught or jammed near the bottom 14. The circular edge between the bottom 14 and the sidewall 16 is rounded for comfort. The base 11 has a main diameter A which is generally constant between the bottom 14 and top 15, except as described herein. The FIGS. illustrate a preferred embodiment in which the sidewall 16 is cylindrical, but in other embodiments, the base 11 may have other shapes, such as having an oval cross-section, triangular cross-section, or some other shape lending to aesthetic or functional qualities.

An annular flange 21 is formed integrally with the sidewall 16 and extends outwardly therefrom proximate to the top 15 of the base 11. The flange 21 extends outwardly from the sidewall 16 generally perpendicular to the sidewall 16. The flange 21 has a diameter B which is greater than the diameter A of the base 11. The portion of the base 11 between the bottom 14 and the flange 21 will be referred to herein for convenience as a grip portion 22.

A cap 23 of the base 11 extends between the flange 21 and the top 15 of the base 11. The cap 23 is an integral mount for receiving the applicator 12 onto the base 11, and an interlock engagement assembly 26 carried between the cap 23 and applicator 12 securely and releasably engages the applicator 12 onto the base 11. The cap 23 aligns the applicator 12 coaxially with the base 11, with the flange 21, and positions the applicator 12 laterally with respect to the flange 21. The cap 23 is generally cylindrical and includes a short sidewall 24 projecting axially away from the flange 21 and a top 25 extending radially inwardly from the sidewall 24 at the top 15 of the base 11. As the term is used herein, "axially" means aligned along an elongate axis X common to the base 11 and the applicator 12, and the term "radially" means aligned transverse to the axis X and directed inwardly to or outwardly from the axis X. The top 25 is formed with a circular opening 30 providing access into the interior 20 of the base 11 through which tension rings 13 can be applied thereto or withdrawn therefrom. The cap 23 is coaxial to the base 11, and the opening 30 is coaxial to both the cap 23 and the base 11. The cap 23 has a diameter C which is less than the diameters A and B of the grip portion 22 of the base 11 and the flange 21, respectively. The cap 23 has a plurality of spaced-apart tabs 31 projecting radially outwards from the sidewall 24. The tabs 31 are each short and have a circumferential width about the sidewall 24. Though not shown in FIG. 1A, there are preferably four tabs 31 formed around the sidewall 24. The tabs 23 are integrally formed to the sidewall 24 of the cap 23. The tabs 23 define an engagement element of the interlock engagement assembly 26, the engagement element being carried on the cap 23 for securing the applicator 12 onto the base 11.

Figure 2A:
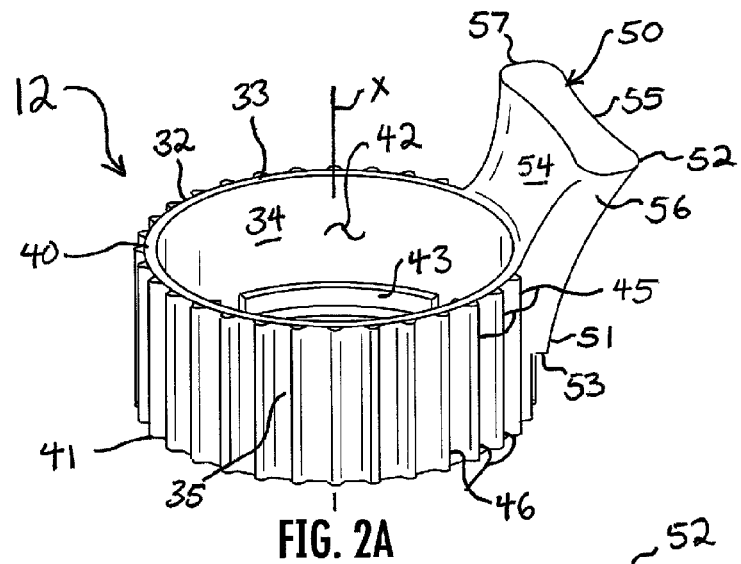
FIGS. 2A, 2B, and 2C are top perspective, side elevation, and top plan views of the applicator of FIG. 1A, respectively.
Figure 2B:
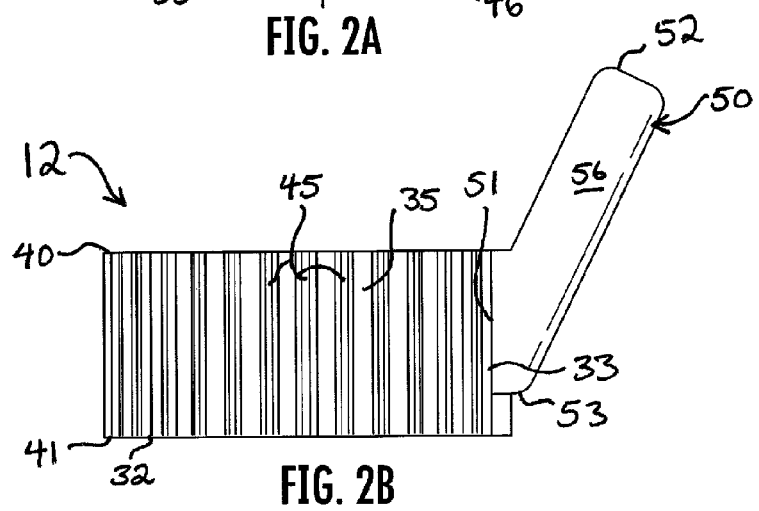
Figure 2C:
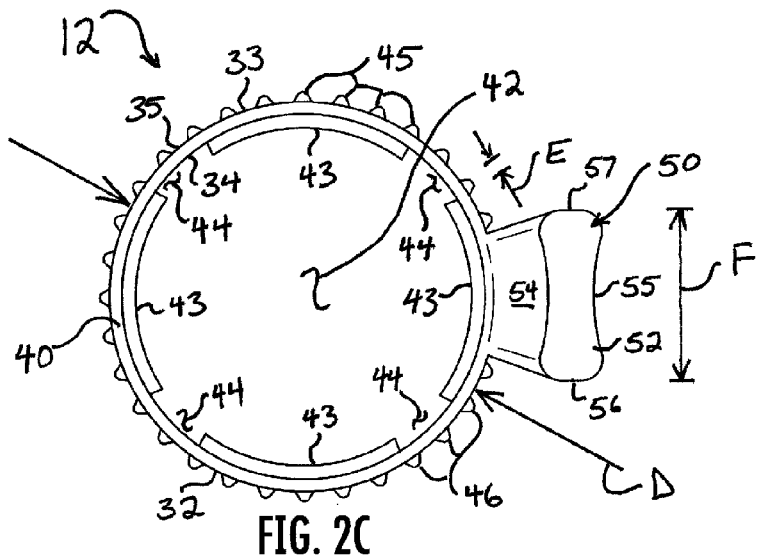

The applicator 12 is shown in more detail in FIGS. 2A, 2B, and 2C, to which reference is now made. As seen in those FIGS., the applicator 12 is a short, generally cylindrical annulus or ring having an outer diameter D. The applicator 12 has a body 32 formed of a continuous cylindrical sidewall 33 having an inner face 34 and an opposed outer face 35. The sidewall 33 extends between a top 40 and a bottom 41 of the body 33 of the applicator 12, such that the sidewall 33 defines the majority of the body 33 of the applicator 12.

The inner face 34 of the sidewall 33 bounds a cylindrical void which is a socket 42 for receiving the cap 23 of the base 11. The inner diameter of the applicator 12 within the inner face 34 closely corresponds to the outer diameter of the cap 23, so that the applicator 12 snugly fits onto the cap 23 of the base 11. Four tabs 43 are integrally formed to the inner face 34 of the applicator 12. The tabs 43 project radially inwardly and are spaced apart by gaps 44, which correspond in width to the tabs 31 on the cap 23 of the base 11. The tabs 43 are each disposed just above the bottom 41 of the applicator 12.

On the outer face 35 of the sidewall 33, a plurality of ribs 45 extend axially with respect to the applicator 12 between the top 40 and bottom 41 of the sidewall 33. The ribs 45 are spaced apart circumferentially along the outer face 35. Each rib 45 has a width E across the outer face 35, and the ribs 45 are spaced apart from each other by approximately that same width E. Each rib 45 is triangular prismatic, having a first long face formed integrally to the outer face 35 of the sidewall 33 and having two opposed, converging faces projecting outwardly from the outer face 35. A crest 46 is formed from a bevel between the converging faces of each rib 45 to dull the edge formed therebetween. Proximate to the top 40 of the applicator 12, each rib 45 is also beveled downward so that the tension ring 13 can be more easily moved over the ribs 45.

Referring still to FIGS. 2A-2C, the applicator 12 further includes a tab 50 projecting upwardly above the top 40 of the sidewall 33. The tab 50 is formed rigidly and integrally to the body 32 of the applicator 12, so that it provides a rigid and resilient lever which can be gripped when applying the applicator 12 onto a penis and unloading the tension ring 13 from the applicator 12 onto the penis, as will be later explained. The tab 50 has a base 51 formed integrally to the sidewall 33 and a top 52 opposed from the base 51. The base 51 is large and extends outward from the sidewall 33 from between the top 40 of the sidewall 33 and just above the bottom 41. The base 51 projects outward from the sidewall 33 so that a shoulder 53 of the tab 50 is formed between the base 51 and the sidewall 33. The shoulder 53 is an inward corner between the tab 50 and the sidewall 33 for catching and retaining the tension ring 13, as will be described later.

The tab 50 is generally prismatic and has two opposed major faces 54 and 55 and two opposed minor faces 56 and 57 transverse to the major faces 54 and 55. The major face 54 is on an inner side of the tab 50, directed toward the body 32 of the applicator 12, thus defining an inner face, and it extends from the top 40 of the sidewall 33 to the top 52 of the tab 50. The minor face 55 is on an outer side of the tab 50, directed away from the body 32, thus defining an outer face, and it extends from the shoulder 53 proximate the bottom 41 of the sidewall 33 to the top 52 of the tab 50. The tab 50 is aligned at approximately five degrees transverse to the elongate base 11 and to the axis X extending through the body 32 of the applicator 12. The major faces 54 and 55 are each concave, into the tab 50, so that the tab 50 has a roughly hourglass cross-sectional shape which enhances gripping the tab 50 between the thumb and forefinger of a user's hand. The concave characteristic of the identical and opposite major faces 54 and 55 assures the user that the applicator 12 is held securely, and promotes a vertical grip. From the base 51 to the top 52 of the tab 50, the minor faces 56 and 57 diverge outwardly away from each other. The minor faces 56 and 57 are separated by a width F of the tab 50 at the top 52, which generally corresponds to the average width of a man's thumb.

Returning to FIG. 1A, a tension ring 13 is disposed above the base 11 and applicator 12 in the exploded view. The tension ring 13 shown is similar to a leading tension ring sold by Timm Medical Technologies, Inc., and known conventionally as a Timm-Osbon model. Briefly, the tension ring 13 has a central annulus 60 constructed a highly resilient rubberized material having low, but some, elasticity. The annulus 60 has an inner diameter G, and is deformed outwardly with a projection on one side, forming a U-shaped notch 61 intended to fit against the bottom of the penis, and forming two "pressure points" 62 on the opposite side of the annulus 60 intended to fit against the top of the penis. Two grasping loops 63 and 64 are formed on opposed sides of the annulus 60. In conventional use of the tension ring 13, the grasping loops 63 and 64 aid in the removal of the tension ring 13 from the penis after intercourse.

Figure 1B:
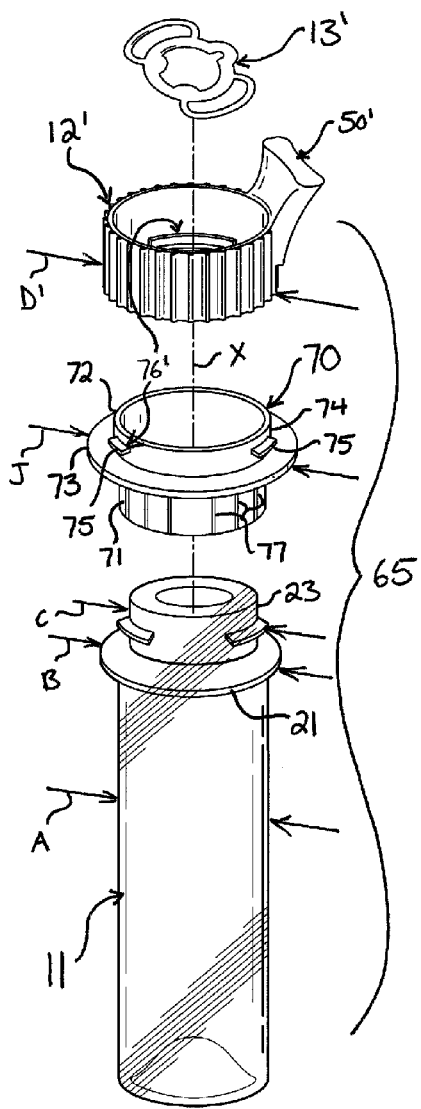
FIG. 1B is an exploded perspective view of a tension ring and an alternate embodiment of a tension ring applicator assembly constructed and arranged according to the principle of the invention.

FIG. 1B illustrates an exploded view of a tension ring applicator assembly, identified with the reference character 65, which is similar to the tension ring applicator assembly 10. The assembly 65 include the same base 11 as in the assembly 10, but includes a larger applicator 12'. The larger applicator 12' is useful for larger tension rings 13' and larger penises. The elements and features of the assembly 65 are identical to those of the assembly 10 in every respect other than in size. As mentioned, the assembly 65 uses the same base 11 but a larger applicator 12'. For clarity, the larger elements and features of the assembly 65 are identified with the same reference characters as those of the smaller counterparts in assembly 10. However, the larger elements and features are marked with a prime symbol ("'") to identify them as larger and being part of the assembly 65 rather than the assembly 10. It should be understood, however, that while the sizes are different, the elements and features are otherwise identical. Because of this, the discussion will not describe those identical elements and features.

The base 11 includes the cap 23 with the same diameters A, B, and C. The applicator 12' has a diameter D' which is greater than the diameter D of the applicator 12. The applicator 12' is too large to fit directly onto the base 11. Therefore, assembly 65 includes an adapter 70 for coupling between the base 11 and the applicator 12'. The adapter 70 is generally cylindrical and has a cylindrical lower sidewall 71, a cylindrical upper sidewall 72, and an annular flange 73 formed therebetween. The lower sidewall 71 has an inner face on which are formed four tabs, identical in construction and placement to the tabs 43 on the applicator 12 shown in FIGS. 1, 2A, and 2C. These tabs engage with and securely hold the adapter 70 to the cap 23 of the base 11 of the assembly 65. The lower sidewall 71 also has an outer face on which widely spaced apart ribs 77 are formed. The upper sidewall has an outer face 74 on which are formed several tabs 75 which project radially outwardly. The tabs 75 are each short and have a circumferential width about the upper sidewall 72. Though not shown in FIG. 1B, there are preferably four tabs 75 formed around the upper sidewall 72. The tabs 75 are integrally formed to the upper sidewall 72 of the adapter 70. The tabs 75 define an engagement element of an interlock engagement assembly 76, the engagement element being carried on the adapter 70 for securing the applicator 12' onto the adapter 70.

The flange 73 is formed integrally to the adapter 70 and extends outwardly from between the lower and upper sidewalls 71 and 72. The flange 73 extends outwardly generally perpendicular to the lower and upper sidewalls 71 and 72. The flange 73 has a diameter J which is greater than the diameter D' of the applicator 12'. Moreover, in embodiments in which the applicator 12' is larger than the applicator 12, the diameter D' is also larger than each of the diameters A, B, and C on the base 11.

Figures 3C, 3D:
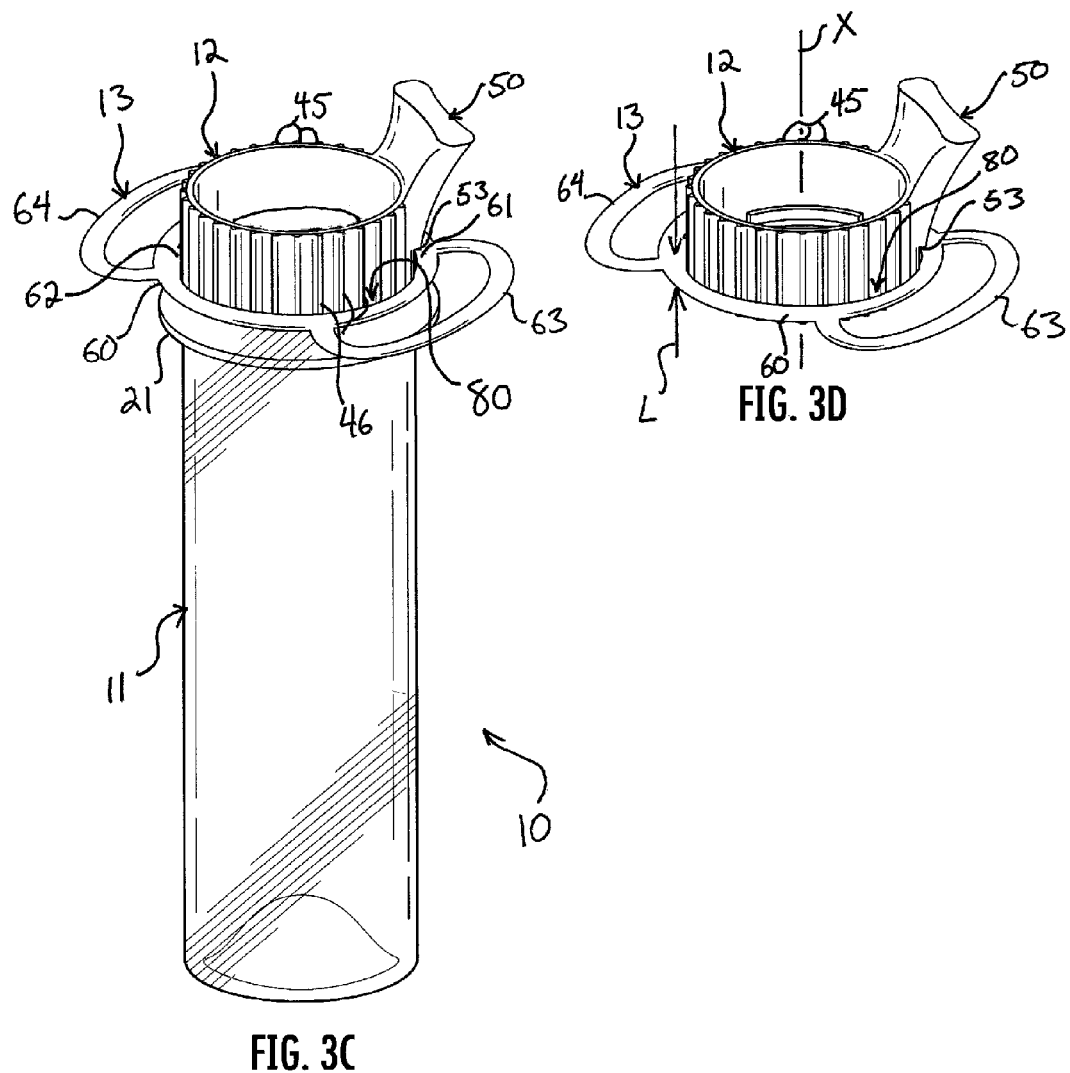

Operation and use of the assembly 10 will now be discussed with reference primarily to FIGS. 3A-3F. It should be understood that operation and use of the assembly 65 will proceed according to a similarly described method, but will include an additional step involving the use of the adapter 70. Without a change in tension ring sizes, once adapter 70 is in place, it may remain so on base 11, ready for future use as described later. It should also be understood that the following discussion of operation of the assembly 10 will be made with reference to the tension ring 13 embodying the conventional Timm-Osbon tension ring model; alternate tension rings will require commensurate modification to the operation described below, as one having ordinary skill in the art will readily appreciate and be able to carry out. In FIG. 3A, the assembly 10 is shown assembled with the applicator 12 in an applied condition thereof. The applicator 12 is applied onto the base 11. The applicator 12 is initially applied to the base 11 by taking the applicator 12 up, such as by hand, aligning it over the cap 23 with the tab 50 directed away from the base 11, registering the gaps 44 between the tabs 43 on the applicator 12 with the tabs 31 on the cap 23 of the base 11, and moving the applicator 12 over and onto the cap 23, thereby seating the applicator 12 on the cap 23 with the cap 23 received in the socket 42 of the applicator 12. The applicator 12 is then rotated in a clockwise or counterclockwise direction several degrees to move the tabs 43 of the applicator 12 into an interference fit under the tabs 31 of the cap 23, thereby binding the tabs 43 and 31 against each other and securing the applicator 12 on the base 11. The applicator 12 is seated on the cap 23, flush against the flange 21, and concealing the cap 23.

In the assembled condition of the applicator 12, the applicator 12 and the base 11 cooperate to define a band or channel 80 formed by and between the applicator 12 and the base 11 which is sized to receive the tension ring 13 therein. The flange 21 bounds the channel 80 on one side, a lower side, of the channel 80, and the shoulder 53 bounds the channel 80 on an opposed, or upper, side of the channel 80. The channel 80 is thus an annular channel formed between the flange 21 and the shoulder 53 of the tab 50. The channel 80 extends circumferentially about the applicator 12 across the ribs 45 of the applicator 12, and the shoulder 53 bounds only a portion of the channel 80 which extends around the sidewall 33 coextensively with the width F of the tab 50, which is less than half the sidewall. The channel 80 shares the outer diameter D of the applicator 12, which diameter D is less than the diameter B of the flange, as shown in FIG. 1A. Thus, the channel is inboard with respect to the flange, and is also inboard with respect to the tab 50.

It is preferable to have already prepared a tension ring 13, either by removing one from the interior 20 before applying the applicator 12 to the base 11, or by obtaining a new one from product packaging. Once the applicator 12 is in the applied condition shown in FIG. 3A, the tension ring 13 may be applied to the assembly 10 pursuant to the following description.

The assembly 10 is gripped by a user 100, whose torso is shown in FIG. 3B. The assembly 10 is placed between both thighs 101 of the user 100, with the tab 50 directed toward the user 100. The assembly is preferably gripped tightly between the thighs 101 of the user 100. By squeezing his thighs 100 against each other with the assembly 10 disposed therebetween, the user 100 can exert a great deal of lateral force to stabilize the assembly 10 and prevent it from tipping, rocking, rotating, or moving in general. The user 100 thus holds the assembly 10 steady with the tab 50 directed toward the user 100 without using his hands. Preferably, only the grip portion 22 of the base 11 is held between the thighs 100, so that the flange 21 and applicator 12 are exposed above the thighs 100.

The user 100 then applies the tension ring 13 onto the applicator 12. He does this by taking up the annulus 60, orienting the U-shaped notch 61 toward the user 100, and moving the annulus 60 of the tension ring 13 over the tab 50. The user 100 may take up the tension ring 13 at the annulus 60 by placing his thumbs oppositely inside the annulus 60. The inner diameter G of the annulus 60 is greater than the width F of the tab 50 at the top 52 of the tab 50, so that the tension ring 13 is easily applied over the tab 50. Nevertheless, the tension ring 13 is stretched slightly to make easier the application of the annulus 60 over the tab 50. If the user 100 chooses to take up the tension ring 13 in his thumbs, spreading his thumbs apart is an easy and effective way to stretch the tension ring 13 slightly.

Once over the tab 50, the tension ring 13 is moved down the tab 50 and fitted under the shoulder 53. A portion or arcuate segment of the annulus 60 of the tension ring 13 including and surrounding the U-shaped notch 61 is fit under the shoulder 53. The portion of the annulus 60 of the tension ring 13 including and surrounding the U-shaped notch 61 is then seated in the shoulder 53 between the tab 50 and the flange 21. Indeed, the user relies on the U-shaped notch 61 being located at the shoulder 53 and tab 50 to ensure proper placement of the tension ring 13 on the applicator 12 for proper placement later of the tension ring 13 on the penis. The grasping loops 63 and 64 are transverse, flanking the tab 50 on the minor faces 56 and 57. Then, while squeezing his thighs together to hold the assembly 10 steady, and with his thumbs placed inside the annulus 60 opposed from each other, the user 100 moves his hands apart from each other and away from his body, thus stretching the annulus 60. The annulus 60 is seated in the shoulder 53, which prevents the side of the annulus 60 including the U-shaped notch 61 from moving; the shoulder 53 acts as a limiter or stop preventing the tension ring 13 from moving off of the applicator 12. The user 100 stretches the opposed side of the annulus 60 over the top 40 of the sidewall 33 of the applicator 12, and then stretches the annulus 60 down to the bottom 41 of the sidewall 33 into the channel 80. The user 100 is prevented from advancing the tension ring 13 off of the applicator 12 because the flange 21 is wider than the sidewall 33 of the applicator 12 and presents a stop. Therefore, as long as the user 100 stretches and moves the tension ring 13 downwardly to the flange 21, the user 100 cannot mistakenly apply the tension ring 13 on the assembly 10.

The tension ring 13 is thus placed in an applied condition on the base 10 and can be removed from between the thighs 101, as seen in FIG. 3C. In the applied condition of the tension ring 13 on the applicator 12, the annulus 60 is seated in the channel, the annulus 60 is stretched over the ribs 45 on the crests 46 of the ribs 45, the U-shaped notch 61 is disposed between the shoulder 53 and the flange 21, and the pressure points 62 are disposed opposite from the tab 50. The tension ring 13 is stretched because the inner diameter G of the tension ring 13 in its relaxed state is less than the diameter D of the applicator 12. The tension ring 13 is therefore tightly held on the crests 46 of the ribs 45 of the applicator 12.

The applicator 12 is then moved into a free condition of the applicator 12, as shown in FIG. 3D. The applicator 12 is easily moved into the free condition thereof by grasping the applicator 12, such as on the outer face 35 or by the tab 50, and rotating the applicator 12 slightly until the tabs 31 of the cap 23 of the base 11 are disposed over the gaps 44 between the tabs 43 on the applicator 12, and the applicator 12 can be simply lifted off the cap 23. When the applicator 12 is placed in the free condition, the tension ring 13 remains carried on the applicator 12 in the channel 80. The channel has a height K (shown in FIG. 3A) which is just greater than a height L of the ring 13, as shown in FIG. 3D.

Figure 3E:
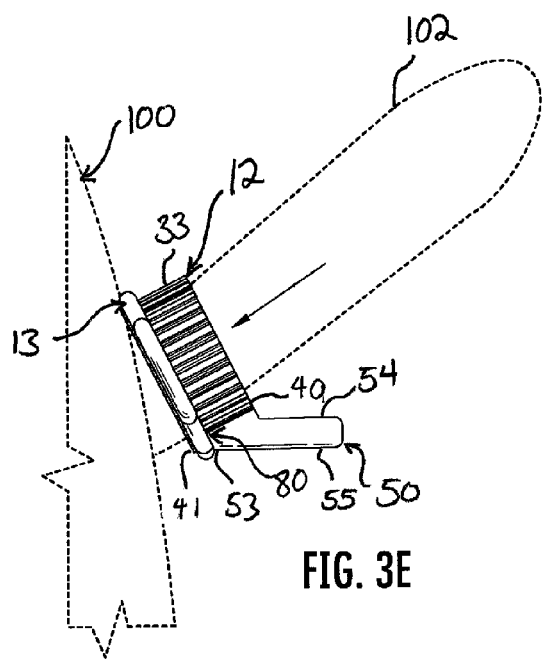

The applicator 12 is then slid over the erect penis 102 of the user 100, as shown in FIG. 3E. The applicator 12 is held and aligned so that the bottom 41 of the sidewall 33 is directed toward the user 100 and the tab 50 is directed away from the user 100. Additionally, the applicator 12 is aligned so that the tab 50 is below the penis 102, thereby registering the U-shaped notch 61 in the tension ring 13 with the bottom of the penis 102 and the pressure points 62 with the top of the penis 102. The applicator 12, together with the tension ring 13, is then moved downward over the penis 102, to the base of the penis 102 and against the user, as shown in FIG. 3E.

Figure 3F:
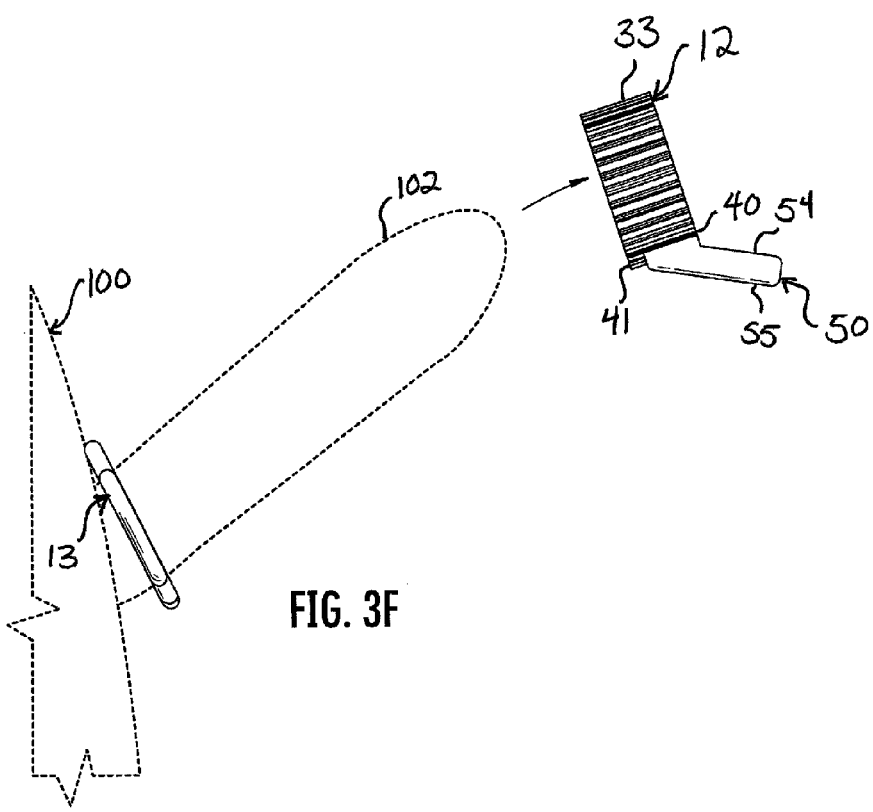

Once the bottom 40 of the applicator 12 is proximate to the user, the applicator is gripped in a preferred gripping arrangement, illustrated in FIGS. 4A and 4B. With reference briefly to those FIGS., the preferred gripping arrangement is characterized by one hand 102 of the user 100 holding or pinching the applicator 12. The hand 102 is oriented vertically, so that it is aligned with the axis X of the applicator 12. The thumb 103 of the user 100 is placed against the major face 54 on the inner side of the tab 50, and the forefinger or index finger 104 is opposed, placed against the major face 55 on the outer side of the tab 50. The thumb 103 and index finger 104 are pinched lightly by the user 100, thus holding the applicator 12 steady at the tab 50. The middle finger 106 of the user 100 is to the side of the tab 50, resting in contact against the sidewall 33 of the applicator 12. The applicator 12 is held steady with the hand 103, with a slight downward force against the base of the penis. This downward force causes the bottom 41 of the sidewall 33 of the applicator on a side opposite the tab 50 to move slightly away from the user. Arranged in this way, the middle finger 106 is the flicked outwardly and downwardly along arcuate line M in FIG. 4B, thereby applying downward force to the tension ring 13 to slide the tension ring 13 off of the applicator 12 and onto the base of the penis, as shown in FIG. 3F. This concurrent application of downward force and sliding force on the tension ring 13 ensures the tension ring 13 readily moves off of the applicator 12. Further, because the height K of the channel 80 is just greater than the height L of the tension ring 13, the tension ring 13 is easily moved off of the bottom 40 of the sidewall 33 of the applicator 12. A personal lubricant, applied to the inner edge of the tension ring 13 when previously preparing and loading the tension ring 13 onto the applicator 12, will reduce friction and therefore the downward pressure required to slide the tension ring 13 off the applicator 12 and onto the penis. The applicator 12 is then slipped off of the penis 102.

Though described above as series of steps, the process of applying the tension ring 13 to the applicator 12 and then to the penis 102 is actually accomplished in a very short period of time, generally only a few seconds with the use of just one hand, when the applicator 12 is pre-loaded, which allows the user 100 to maintain his erection during the application process without fear that his erection or the sexual experience will fade before the tension ring 13 can be applied. In many situations, it may be preferable to pre-load the applicator before the sexual experience, by applying the tension ring 13 to the applicator 12 and then removing the applicator 12 with the tension ring 13 carried on it. In this way, the applicator 12 and tension ring 13 can be kept ready and available for application to the penis 102; application to the penis 102 thus takes only a few seconds, such as less than five seconds, when the applicator 12 is pre-loaded.

As mentioned above, operation and use of the assembly 65 proceeds according to a similarly described method, but includes an additional preparatory step involving the use of the adapter 70. Instead of the applicator 12 being applied directly to the base 11, the user 100 will first apply the adapter 70 to the base 11 and then apply the applicator 12' to the adapter 70. The adapter 70 is applied to the base 11 in a similar method as the applicator 12 is applied to the base 11 in the assembly 10, namely, the adapter 70 is taken up, such as by hand, and aligned over the cap 23. The adapter 70 is then moved over and onto the cap 23, thereby seating the adapter 70 on the cap 23. The adapter 70 is then rotated in a clockwise or counterclockwise direction to move the tabs of the adapter 70 under the tabs 31 of the cap 23, thereby binding the tabs of the adapter 70 and the tabs 31 against each other and securing the adapter 70 on the base 11. The applicator 12' is then applied to the adapter 70. The applicator 12' taken up, such as by hand, and aligned over the adapter 70 with the tab 50' directed away from the base 11, registering the gaps 44' between the tabs 75 on the applicator 12' with the tabs 75 on the upper sidewall 73 of the adapter 70, and moving the applicator 12' over and onto the upper sidewall 72, thereby seating the applicator 12' on the upper sidewall 72 of the adapter 70 with the upper sidewall 72 received in the socket 42' of the applicator 12'. The applicator 12' is then rotated in a clockwise or counterclockwise direction to move the tabs 43' of the applicator 12' under the tabs 75 of the adapter 70, thereby binding the tabs 43' and 75 against each other and securing the applicator 12' on the adapter 70 and the base 11 concurrently. Use of the assembly 65 then proceeds according to the description above.

The present invention is described above with reference to a preferred embodiment. However, those skilled in the art will recognize that changes and modifications may be made in the described embodiment without departing from the nature and scope of the present invention. To the extent that such modifications and variations do not depart from the spirit of the invention, they are intended to be included within the scope thereof.

Having fully and clearly described the invention so as to enable one having skill in the art to understand and practice the same, the invention claimed is:

1. An assembly for applying a tension ring to a penis, the assembly comprising:
   a base having a bottom, an opposed top, a sidewall extending therebetween, and a flange extending outward from the sidewall proximate to the top;
   an applicator configurable between an applied condition releasably coupled to the top of the base and a free condition away from the base;
   the applicator has a bottom, an opposed top, and a sidewall extending therebetween and bounding an open interior sized to receive a penis;
   in the applied condition of the applicator, the applicator and the base cooperate to define a channel formed by and between the applicator and the base which is sized to receive the tension ring therein for application to the applicator; and
   in the free condition of the applicator, the applicator is available to be slid over a penis while carrying the tension ring for application of the tension ring to the penis.

2. The assembly of claim 1, wherein:
   the base is cylindrical;
   the base has a first diameter which is constant from the bottom to the flange;
   the base has a second diameter which is constant from the flange to the top and is less than the first diameter; and
   the flange of the base has a third diameter which is greater than each of the first and second diameters.

3. The assembly of claim 1, wherein:
   the applicator has a tab projecting upwardly from the sidewall of the applicator;
   the tab has a base formed to the sidewall of the applicator and a top; and
   the base of the tab is formed to the sidewall of the applicator above the bottom of the applicator, forming a shoulder.

4. The assembly of claim 3, wherein the channel is an annular, circumferential channel formed between the flange on the base and the shoulder of the tab on the applicator.

5. The assembly of claim 3, wherein:
   the tab has an inner major face directed radially inward toward the applicator;
   the tab has an outer major face directed radially outward away from the applicator; and
   the inner and outer major faces are each concave.

6. The assembly of claim 5, wherein:
   the tab has a first dimension generally aligned across the inner and outer major faces;
   the first dimension is less than an inner diameter of the tension ring; and
   the applicator has an outer diameter which is greater than the inner diameter of the tension ring.

7. The assembly of claim 1, wherein the sidewall of the applicator is formed with ribs projecting outwardly.

8. The assembly of claim 7, wherein the ribs are axially aligned with respect to the applicator.

9. The assembly of claim 1, wherein:
   the base has an interior accessible through an opening at the top; and
   the sidewall of the base is transparent.

10. The assembly of claim 1, further comprising:
    a second applicator sized larger than the applicator; and
    an adapter for coupling the second applicator to the base.

11. An assembly for applying a tension ring to a penis, the assembly comprising:
    a cylindrical base having an elongate grip portion, an opposed cap, and a flange formed therebetween, the flange having a wider dimension than each of the grip portion and the cap;
    an applicator having a bottom, a top, a sidewall bounding an open interior, a tab projecting upwardly from the sidewall to above the top of the applicator, and a shoulder formed between the tab and the sidewall;
    the applicator is configured for movement between an applied condition on the cap of the base, flush against the flange, and a free condition removed from the base; and
    in the applied condition of the applicator, the applicator and the base cooperate to define a channel;
    wherein a portion of the channel extending around less than half the sidewall is bounded by the shoulder.

12. The assembly of claim 11, wherein:
    the base has a first diameter which is constant along the grip portion;
    the base has a second diameter which is constant along the cap and is less than the first diameter; and
    the flange of the base has a third diameter which is greater than each of the first and second diameters.

13. The assembly of claim 12, wherein the sidewall of the applicator is formed with ribs projecting outwardly.

14. The assembly of claim 13, wherein the ribs are axially aligned with respect to the applicator.

15. The assembly of claim 12, wherein:
    the tab on the applicator has a base formed to the sidewall; and
    the base of the tab is formed to the sidewall above the bottom of the applicator, defining the shoulder.

16. The assembly of claim 15, wherein:
    the tab has an inner major face directed radially inward toward the applicator;
    the tab has an outer major face directed radially outward away from the applicator; and
    the inner and outer major faces are each concave.

17. The assembly of claim 16, wherein:
    the tab has a first dimension generally aligned across the inner and outer major faces;

the first dimension is less than an inner diameter of the tension ring; and the applicator has an outer diameter which is greater than the inner diameter of the tension ring.

18. The assembly of claim 11, further comprising:

a second applicator sized larger than the applicator; and an adapter for coupling the second applicator to the base.

19. A method of applying a tension ring to a penis of a user having two thighs and two hands, the tension ring including a central annulus and two opposed grasping loops, the method comprising the steps of:

providing an assembly including a base having a bottom and a top, and an applicator releasably applied to the top of the base, the applicator having a sidewall and a tab formed on the sidewall, the tab defining a channel formed between the applicator and the base;

placing the assembly between the thighs with the applicator exposed above the thighs;

stabilizing the assembly by squeezing the thighs together with the base therebetween;

applying the annulus of the tension ring over the tab;

fitting a portion of the annulus of the tension ring into the channel defined between the applicator and the base;

pulling the annulus over the sidewall of the applicator;

seating the annulus in the channel;

removing the applicator from the base;

sliding the applicator over the penis; and removing the tension ring from the applicator onto the penis.

20. The method of claim 19, wherein the step of placing the assembly between the thighs further comprises orienting the assembly with the tab on the applicator directed toward the user.

21. The method of claim 19, wherein the step of pulling the tension ring over the sidewall of the applicator further comprises aligning the tension ring with the opposed grasping loops flanking the tab of the applicator.

22. The method of claim 19, wherein the step of sliding the applicator over the penis further comprises orienting the applicator with the tab directed away from the user.

* * * * *